US 9,569,828 B2

(12) United States Patent
Munck et al.

(10) Patent No.: US 9,569,828 B2
(45) Date of Patent: Feb. 14, 2017

(54) METHOD AND APPARATUS FOR THE IMAGING OF A LABELED BIOLOGICAL SAMPLE

(71) Applicants: Sebastian Munck, Heverlee (BE); Wim Annaert, Kontich (BE); Patrik Verstreken, Blanden (BE)

(72) Inventors: Sebastian Munck, Heverlee (BE); Wim Annaert, Kontich (BE); Patrik Verstreken, Blanden (BE)

(73) Assignees: VIB VZW, Ghent (BE); Katholieke Universiteit Leuven, K.U., Leuven (BE)

( * ) Notice: Subject to any disclaimer, the term of this patent is extended or adjusted under 35 U.S.C. 154(b) by 276 days.

(21) Appl. No.: 13/661,364

(22) Filed: Oct. 26, 2012

(65) Prior Publication Data
US 2014/0118524 A1   May 1, 2014

Related U.S. Application Data

(63) Continuation-in-part of application No. PCT/EP2011/056784, filed on Apr. 28, 2011.

(30) Foreign Application Priority Data

Apr. 28, 2010  (GB) .................................. 1007055.5

(51) Int. Cl.
*G06T 5/50* (2006.01)
*G02B 21/00* (2006.01)
(Continued)

(52) U.S. Cl.
CPC ............. *G06T 5/50* (2013.01); *G06K 9/00134* (2013.01); *G06T 2207/10064* (2013.01);
(Continued)

(58) Field of Classification Search
CPC .............. H04N 13/00; G01J 1/58; G01J 3/30; G06T 5/50; G03B 42/08; A61B 6/00; G01N 33/558
(Continued)

(56) References Cited

U.S. PATENT DOCUMENTS 4,542,459 A     9/1985 Riederer
6,061,476 A *   5/2000 Nichani ..................... 382/270
(Continued)

FOREIGN PATENT DOCUMENTS

JP   2000-325295   11/2000
JP   2002-286641   10/2002
(Continued)

OTHER PUBLICATIONS

Abbe E: "Contributions to the theory of the microscope and the microscope perception," Arch Mikr Anat vol. 9, pp. 413-468.
(Continued)

*Primary Examiner* — Sath V Perungavoor
*Assistant Examiner* — Patricia I Young
(74) *Attorney, Agent, or Firm* — 24IP Law Group; Timothy R DeWitt

(57) ABSTRACT

A method and apparatus for the imaging of a labeled biological sample. The method comprises illuminating the labeled biological sample, generating members of a time series of images if the labeled biological sample, generating a plurality of difference images between later members of the time series of images of earlier members of the time series of images and combining the plurality of difference images to generate a final image of the labeled biological sample.

15 Claims, 6 Drawing Sheets

(51) Int. Cl.
 G02B 21/16 (2006.01)
 G06K 9/38 (2006.01)
 G06K 9/00 (2006.01)
(52) U.S. Cl.
 CPC ........... G06T 2207/20224 (2013.01); G06T 2207/30024 (2013.01); G06T 2207/30096 (2013.01)
(58) Field of Classification Search
 USPC .......... 348/79, 46; 250/458.1, 584; 382/270, 382/145, 149; 600/476
 See application file for complete search history.

(56) References Cited

U.S. PATENT DOCUMENTS

| 6,909,105 | B1 | 6/2005 | Heintzmann | |
|---|---|---|---|---|
| 2002/0013531 | A1* | 1/2002 | Hayashi | 600/476 |
| 2005/0253088 | A1 | 11/2005 | Hattori | |
| 2007/0057199 | A1 | 3/2007 | Richardson | |
| 2007/0057211 | A1* | 3/2007 | Bahlman et al. | 250/584 |
| 2008/0070323 | A1 | 3/2008 | Hess | |
| 2009/0242798 | A1* | 10/2009 | Bewersdorf et al. | 250/458.1 |
| 2013/0126759 | A1 | 5/2013 | Betzig et al. | |

FOREIGN PATENT DOCUMENTS

| JP | 2004-184379 | 7/2004 |
|---|---|---|
| JP | 2006-187598 | 7/2006 |
| JP | 2007-222073 | 9/2007 |
| JP | 2008-542826 | 11/2008 |
| JP | 2009-503442 | 1/2009 |
| WO | 2007009812 | 1/2007 |
| WO | 2010/015563 A1 | 2/2010 |

OTHER PUBLICATIONS

Nasset MJ, Woehl JC: "Realistic modelling of the illumination point spread function in confocal scanning optical microscopy," J. Opt. Soc. Am. A vol. 27, 2010, pp. 295-302.
R. J. Kittel et al. "Bruchpilot Promotes Active Zone Assembly, Ca2+ Channel Clustering, and Vesicle Release," Science vol. 312, May 19, 2006, p. 1051.
Kasprowicz et al., "Inactivation of clathrin heavy chain inhibits synaptic recycling but allows bulk membrane uptake," J Cell Biol vol. 182, Sep. 8, 2008, p. 1007.
W. Fouquet et al., "Maturation of active zone assembly by Drosophila Bruchpilot ," J Cell Biol vol. 186, Jul. 13, 2009, p. 129.
Spasic et al., "Rer1p competes with APH-1 for binding to nicastrin and regulates γ-secretase complex assembly in the early secretory pathway," J Cell Biol vol. 176, 2007, pp. 629-640.
Cardenas et al., "Golgi localisation of GMAP210 requires two distinct cis-membrane binding mechanisms," DMC Biol. vol. 7, 2009, p. 56.

* cited by examiner

METHOD AND APPARATUS FOR THE IMAGING OF A LABELED BIOLOGICAL SAMPLE

CROSS-REFERENCE TO RELATED APPLICATIONS

The present application is a continuation-in-part of PCT Application PCT/EP2011/056784 filed on Apr. 28, 2011, which claims priority to and benefit of UK Patent Application No. GB 1007055.5 filed on Apr. 28, 2010.

The aforementioned applications are hereby incorporated by reference in their entirety.

BACKGROUND OF THE INVENTION

Field of the Invention

The field of the present invention relates to a method, an apparatus and a computer program product for the imaging of a labeled biological sample.

Brief Description of the Related Art

A number of so-called "super-resolution" imaging technologies have recently emerged. These super-resolution imaging technologies include stimulated emission depletion (STED), photo-activated localization microscopy (PALM) and stochastic optical reconstruction microscopy (STORM). These super-resolution imaging technologies enable the imaging of labeled biological samples, by separating the emission of fluorophore labels attached to the biological samples in space or time, thus overcoming the resolution limit of conventional light microscopes. Methods like PALM and STORM activate only a few of the fluorophore labels, followed by fitting. These methods assume that the emission (fluorescence) comes from a single point. STED achieves this by turning of neighboring ones of the emitters (fluorophores) by using a second, donut-shaped STED laser. Such prior art methods therefore localize only single labeled molecules or use a spatially non-uniform illumination and a non-linear photo-response. Given the impact on biological research, the super-resolution imaging technology has thus gained great attention. Assembly of a super-resolution device and running the super-resolution device or acquiring an integrated solution can be expensive and customized systems have been shown to currently outperform commercial ones.

Confocal laser scanning microscopy is one example of a method for obtaining high resolution optical images of a complex object with a degree of depth selectivity. The complex object can be, but is not limited to, a biological specimen. The optical images of the complex object are acquired by a photo-detection device and are subsequently reconstructed by a computer. This computer reconstruction allows a generation of a 3-D reconstruction of the complex object.

In a confocal laser scanning microscope, a laser light beam passes through an aperture and the laser light beam is subsequently focused by an objective lens into a small volume within or onto a surface of the biological specimen. The biological specimen may be labeled with a fluorophore such as fluorescent molecules, antibodies or fluorescent particles. Labeling of the biological specimen with the fluorophore is particularly common for biological applications of microscopy. Scattered and reflected laser light as well as any fluorescent light from the fluorophore of the labeling of the biological specimen is collected by the objective lens. Consequently a beam splitter separates the collected light based on its spectral characteristic. The collected light is than detected by a sensor, such as a light sensitive device. This light sensitive device used in confocal microscopy is typically a point detector such as a photo-multiplier. In a spinning disk microscope the light sensitive device can be a charge coupled device (CCD). Moreover in front of the light sensitive device there may be a filter to allow selective passage of light with a specific fluorescent wavelength whilst blocking the laser light beam of the original wave length (i.e. the scattered and reflected laser light). The light sensitive device transforms the light signal into an electrical signal that is passed to a computer where the electrical signal is stored in an image memory in the computer.

Several examples of imaging systems are known in the art in which a time series of images are made of a particular object and difference images are generated. For example, U.S. Pat. No. 4,542,459 teaches a matched filter for x-ray hybrid subtraction in which low energy and high energy x-ray exposures are made before and after an injected x-ray contrast medium arrives at a blood vessel of interest. The '459 patent teaches two different procedures for obtaining a sequence of x-ray images that yield signals or data representative of a hybrid subtraction image. The method of '459 can be used to eliminate signals due to bone and ensure that signals representative of the blood vessel filled with the x-ray contrast medium remain.

U.S. Pat. No. 6,061,476 teaches a method to detect an object in which two images are taken of a particular object at a different time and one image is subtracted from the other image. The resulting subtracted image is separated into two components: a positive difference image and a negative difference image. The two components are processed to determine whether—the object is present or not. In the example given in the '476 patent, the method is used to inspect solder paste as to whether the object mayor may not be present.

SUMMARY OF THE INVENTION

A method for the imaging of labeled biological samples is disclosed. The method comprises illuminating the labeled biological samples over a period of time. A time series of images of the labeled biological samples is then generated and a plurality of difference images between later members of the time series images and earlier members of the time series of images is generated. The difference images are then combined to produce a final image of the labeled biological sample.

The method enables the generation of an image, which has a greater resolution (around 100 nm) than provided for by prior art methods based on prior art confocal or wide-field microscopy.

The method of this disclosure enables sub-diffraction imaging far beyond the point where two emitters, i.e. labels attached to the biological sample, are in such close proximity that the two emitters form a single indiscernible diffraction pattern as described by the Sparrow limit. The approach described in this disclosure is based on extracting spatial information from imaging the same region multiple times to obtain the time series of images, thus bleaching the fluorophores. An image normally obtained in a single scan is thus "separated" into multiple ones of a series of images. From this series of images, positional information of an underlying structure of the biological sample can be extracted by processing the series of images to form the difference images and detecting local bleached fluorescence maxima of the emitters. Multiple ones of the series of images are than combined to construct a "super-resolved" image. The processing of the difference images enables the reconstitutions and localization of the underlying structures better than if all of the emitters are imaged simultaneously. The method enables enhanced resolution on existing microscopes (i.e. without customization) and is applicable to multiple detection channels.

The unambiguous identification of single ones of the emitters is not required for the method (unlike in pointillistic approaches, such as the PALM and STORM methods, discussed above). Therefore different bleach rates of the multiple emitters per position can be used. The method of the present disclosure enables super-resolution similar to existing methods but obviates the need for specialized instrumentation, specialty tailored labels or single molecule accuracy while allowing for multi-channel experiments.

The method of the disclosure does not require the imaging of a single labeled molecule or non-uniform photo-illumination. There is no requirement for specially tailored fluorophores as the emitters. The method does not require repeatedly blinking ones of the emitters and is therefore different than the fluctuation analysis used in prior art methods like super-resolution optical fluctuation imaging (SOFI). The method of the disclosure preserves brightness relations within areas of the imaged biological sample.

The method of the disclosure also has no need for a spatially-controlled saturated fluorophore depletion, such as that known from the STED methods or methods involving saturated excitation of the emitters.

In one aspect of the disclosure a mathematical filter can be applied to the difference images in order to improve the resolution of the generated final image. The mathematical filter is a high pass filter, such as but not excluding a Top-hat or a Mexican-hat filter. The mathematical filter can also be a deconvolution filter.

The labeled biological samples are generally illuminated from an excitation light source, such as a laser. The excitation light source excites the fluorophores used as the labels to produce fluorescence.

In a further aspect of the disclosure, it is possible to combine the generated final image together with a 3-D image of the labeled biological sample in order to generate a composite 3D image of the biological sample.

An apparatus for the imaging of labeled biological samples is also disclosed. The apparatus comprises an illumination source for illuminating at least a portion of the labeled biological sample and a detection device for detecting radiation from the labeled biological sample. The apparatus further includes an image memory, which stores members of a time series of images generated by the detection device and an image processor. The image processor is adapted to generate a plurality of difference images between later members of the time series images and earlier members of the time series images. The image processor combines the plurality of difference images in order to generate a final image of the labeled biological sample.

The apparatus can be a confocal laser scanning microscope or a wide-field microscope.

The image processor can include a high pass filter, such as, but not limited to, the Top-hat filter or the Mexican-hat filter. Other types of filters, such as deconvolution filters, can be used without limitation.

A computer program product for the imaging of labeled biological samples is also disclosed. The computer program product comprises of a non-transitory computer readable medium having a control logic stored therein for causing a scanning confocal microscopy to execute the method for the imaging of the labeled biological samples.

The method and apparatus of the disclosure can find numerous applications in investigations into the structure and behavior or biological systems. The method and apparatus can also be used in surgical and diagnostic procedures.

DESCRIPTION OF THE FIGURES

For a more complete understanding of the present invention and the advantages thereof, reference is now made to the following description and the accompanying drawings, in which:

In FIG. 3 A the scale bar is 100 nm.

In FIG. 4A, 4K, 4L the scale bar is l/lm. In FIG. 4M the scale bar is 100 nm. In FIGS. 4P and 48 the scale bar is 200 nm. FIG. 4G shows a 3-D representation. FIGS. 4H to 4I show live imaging of GFP-tagged doublecortin (DCX).

DETAILED DESCRIPTION OF THE INVENTION

The present invention will now be described on the basis of the drawings. It will be understood that the embodiments and aspects of the invention described herein are only examples and do not limit the protective scope of the claims in any way. The invention is defined by the claims and their equivalents. It will be understood that features of one aspect or embodiment of the invention can be combined with a feature of a different aspect or aspects and/or embodiments of the present invention.

Figure 1:
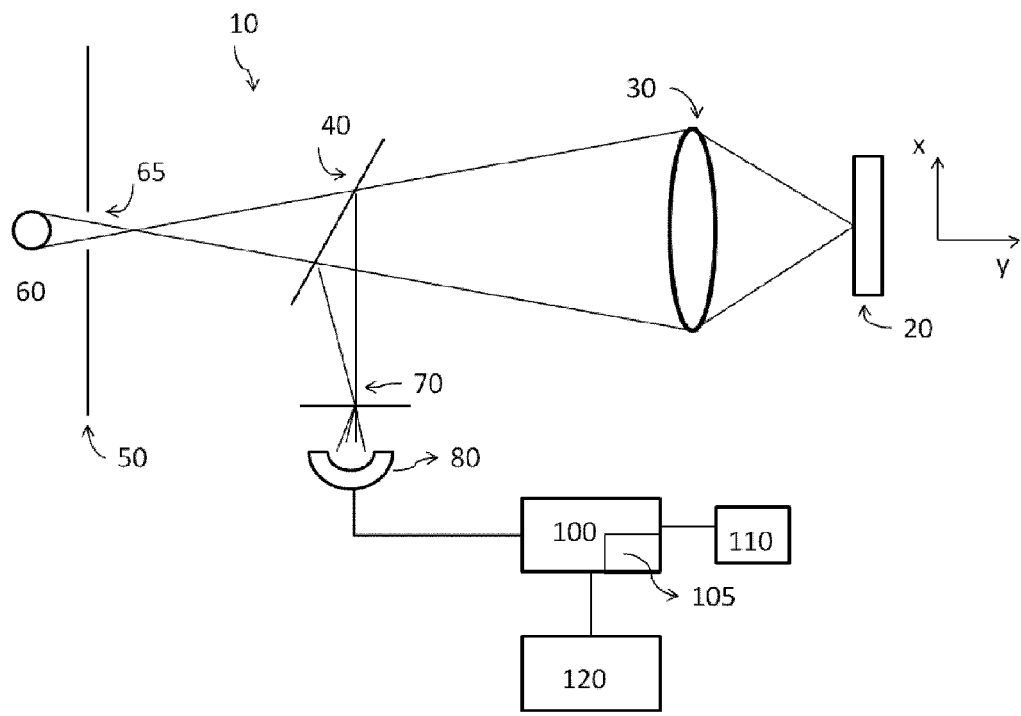
FIG. 1 shows an example of an apparatus according to an aspect of the present disclosure.

FIG. 1 shows an example of an apparatus according to an aspect of the present invention, in particular a microscope 10. A biological sample 20 is illuminated by a light 65 that is emitted from an excitation light source 60. The light 65 passes through a first aperture 50 to an objective lens 30. The objective lens 30 is used to illuminate and focus the light 65 onto the biological sample 20.

The term "biological sample" or "biological specimen" as used in this disclosure refers to a complex sample and means a sample with biological material taken from a biological source, for example from human or animal subjects, plants, bacteria, viruses, yeasts, fungi, etc. The term biological sample includes, without the purpose of being limitative, organs, organelles, tissues, body fluid, cells, cultures of tissues or cells, as well as supernatants and rinses thereof. A biological sample also encompasses molecules such as polysaccharides, nucleic acids, proteins, peptides, lipids, and parts derived thereof. The biological sample may also be obtained by subjecting the biological sample to a pre-treatment if necessary, for example, by homogenizing or extracting. Such a pre-treatment may be selected appropriately by those skilled in the art depending on the biological sample to be subjected. The present disclosure also encompasses biological samples, such as a tissue sample from the human or animal body including, without being limitative, buccal cells, a brain sample, a skin sample, organ sample, placental tissue, fetal cells or any other source of cells that are obtainable thereof. The present disclosure also encompasses biological samples such as a fluid from the human or animal body. Particularly, the sample can be whole blood, blood plasma, blood serum, cerebral fluid, sputum, stool, biopsy specimens, bone marrow, oral rinses, tissues, urine or mixtures thereof.

The term 'labeled biological sample' used in the present disclosure is intended to encompass any type of the biological sample 20 that includes a detectable label. The biological sample 20 may be labeled with a particle (not shown) which functions as the detectable label. The detectable label could be, but is not limited to, an enzyme, a fluorophore, a fluorescent dye, an electromagnetic label or a radioactive label. In an aspect of the disclosure the detectable label used on the labeled biological sample 20 is a fluorophore and the excitation light source 60 is a laser. The excitation light source 60 emits light with a wave length adapted to cause the detectable label (i.e. fluorophore) in the labeled biological sample 20 to fluoresce. It is to be appreciated that the excitation light source 60 is not limited to a laser, and any light source 60 that renders the labeled biological sample 20 visible can be used as the light source 60.

Non-limiting examples of labels are provided further herein (see also the examples below). According to particular examples, the biological sample 20 may carry more than one detectable label. Therefore the biological sample may have two, three or more detectable labels, as will be discussed below. The detectable labels may be identical labels (e.g. to strengthen the signal). The detectable labels may be different to one another but of the same nature (e.g. two different fluorescent labels), may be of a different nature (e.g. a fluorescent and an electromagnetic label) or combinations thereof (e.g. two identical fluorescent labels and a third different fluorescent label).

The light 65 is scattered and reflected as well as being fluoresced from the labeled biological sample 20. The light 65 is also collected by the objective lens 30 and passed to a beam splitter 40. The beam splitter 40 separates the scattered, reflected and fluoresced light and passes the scattered, reflected and fluoresced light through a second aperture 70 to a photo 2 detection device 80. The photo detection device 80 could be one of a photo multiplier tube, an avalanche photo diode, a complementary metal oxide semiconductor device (CMOS) or a charge-coupled device. A filter (not shown) may be placed in front of the photo detection device 80 to remove light of certain wavelengths, such as the scattered light and the reflected light (but not fluoresced light). The photo detection device 80 converts a light signal received by the photo detection device 80 to an electrical signal that is passed to a computer 100.

The computer 100 has an image memory 110 connected to the computer 100 and a display 120 on which images of the labeled biological sample 20 can be displayed (or printed). The computer 100 further includes an image processor 105. The image processor 105 may be either a specialized image processor or a conventional processor in the computer 100 and the image processor is configured to process images of the labeled biological sample 20.

In one aspect of the present invention the biological sample 20 can be moved in a planar manner (shown as the x-y axis in FIG. 1) while the light source 65 remains stationary. Typically the biological sample 20 is mounted onto a stage (not shown), which can be moved such that the light 65 falling on a surface of the biological sample 20 is scanned over the surface and/or the volume of the biological sample 20. In an alternative aspect the light source 60 can be moved in a planar manner (shown as the x-y axis in FIG. 1) while the labeled biological sample 20 remains stationary.

The photo-detection device 80 records the light signals from the illuminated portion of the labeled biological sample 20. The photo-detection device 80 then passes the recorded light signals as electrical signals to the computer 100 where the image of the illuminated portion of the labeled biological sample 20 is stored in the image memory 110. As is known in the art, the plurality of image portions in the image memory 110 of the labeled biological sample 20 can be combined to form a single image of the labeled biological sample 20.

It is further possible to include feedback loops in the apparatus 10 to adjust, for example, the exposure time, the gain, the power of the light source 60 and/or other settings of the microscope. These feedback loops can be implemented in the computer 100.

Figure 2:
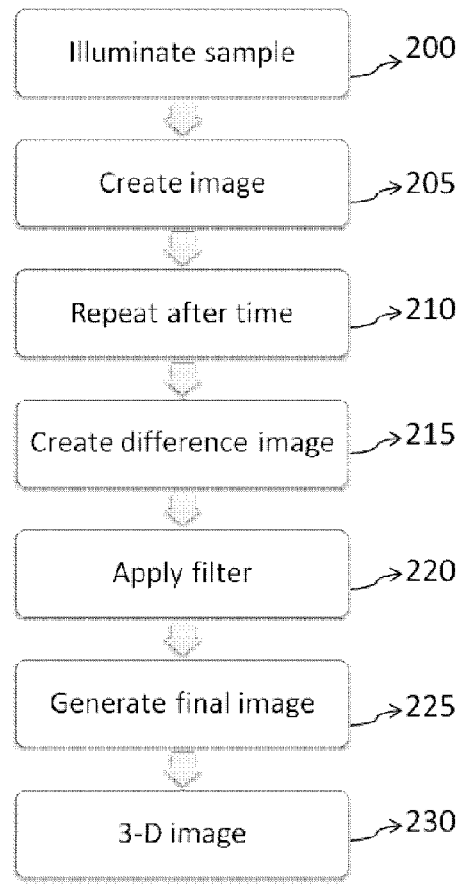
FIG. 2 shows an overview of the method according to an aspect of the present disclosure.

The improvement for the imaging of the labeled biological sample 20 will now be explained in connection with a method for the imaging of the labeled biological sample 20 as shown with reference to FIG. 2.

In step 200 the labeled biological sample 20 is illuminated with the light 65 from the light source 60. The labeled biological sample 20 is moved on the stage such that the light 65 successively illuminates all portions of interest on the surface of the labeled biological sample 20.

In step 205 a first member of a time series of images of the labeled biological sample 20 is created from the light signals recorded by the photo detection device 80 in the image memory 110.

In step 210 a further image is created of the portions of interest of the labeled biological sample 20. The further image is typically created by taking images at a rate of two frames per second.

A further set of images is then repeatedly created in step 210. The further set of images is repeatedly created after every period of time (for example at a rate of two frames per second) until a reasonable number of members of a time series of images is created. The number of images created depends on a number of factors, as will be explained later. Typically up to several hundred images are created of the time series of images.

In step 215 a series of difference images of the labeled biological sample 20 are created. This series of difference images of the labeled biological sample 20 is done by selecting an image and the next or sequential image in the time series. The image processor 105 in the computer 100 compares the next or sequential images and creates a difference image. The creation of the difference image can be carried out by comparing the intensities of the pixels in each one of the images.

The results of the series of difference images can be stored in the image memory 110.

It will also be appreciated that there may be situations under which non-sequential images in the time series will be compared to one another to create the difference image or wherein differential images are normalized with respect to the maximum intensity and a filter for estimating the noise (e.g. Kalman) is used. It will be appreciated that if the differential images are not normalized there would be an inherent bias towards the first (stronger) image. It would also be possible to normalize over the total number of pixels.

The individual fluctuations in the intensity of the radiated light are chiefly caused by photo-physical events, for example photo-conversion or fluorophore bleaching. These photo-physical events result in a localized reduced intensity in successive ones of the series of images. The individual fluctuation, such as increased localized intensities, may be caused by hemophilic fluorescence resonance energy transfer that quantizes fluorescence, shot noise and dye blinking (resulting from the detectable label) in the labeled biological samples 20. These photo-physical events are associated with the fluorescence of individual molecules in the labeled biological sample 20 and can thus contribute to the accurate localization of the individuated molecules within the image.

A mathematical filter is applied to the series of difference images in step 220. The mathematical filter applied is typically a high pass filter which is intended to filter for higher spatial frequencies and emphasizes differences in the difference images created in the step 215 to provide filtered difference images. This results in an enhancement of the peaks of the photo-bleaching whilst reducing the noise in the difference images.

The filtered difference images are then added together in step 225. The addition of the filtered difference images generates a final image of the labeled biological sample 20 which can then be displayed on the display device 120 or can be further processed. The addition of the filtered difference images can be described by the following equation:

$$I_{reconstructed} = \text{filter} \sum_{i=1}^{n-1} \left( \text{filter} \sqrt{(I_{(xy)i} - I_{(xy)i+1})^2} \right) \quad (1)$$

Where $I_{(reconstructed)}$ is the final generated image. $I_{(xy)}$ are members of the set of images taken at time t. n is the total number of images.

For the filtering steps the following Top-hat mathematical filter was exemplary used:

$$\begin{matrix}
0 & 0 & -1 & -1 & -1 & 0 & 0 \\
0 & -1 & -1 & -1 & -1 & -1 & 0 \\
-1 & -1 & 3 & 3 & 3 & -1 & -1 \\
-1 & -1 & 3 & 4 & 3 & -1 & -1 \\
-1 & -1 & 3 & 3 & 3 & -1 & -1 \\
0 & -1 & -1 & -1 & -1 & -1 & 0 \\
0 & 0 & -1 & -1 & -1 & 0 & 0
\end{matrix}$$

One example of further processing is to combine the final image with an image generated by conventional confocal laser scanning microscopy in order to generate a 3-D image of the labeled biological sample 20.

The method of the present invention can be executed by a computer program product which can be incorporated into existing microscopes.

In the examples described below photo-bleaching is used as the photo-physical effect. It will be understood that other photo-physical effects can be used and/or the photo-physical effects may be combined with each other. It will be furthermore appreciated that not all of the labeled biological sample 20 needs to be illuminated. It is possible to use arbitrary patterns of illumination.

It will be understood that there may be more than one label attached to the labeled biological sample 20. In other words, there is a certain degree of redundancy as is known in the prior art. For example a secondary antibody produced by Invitrogen has five multiple fluorophores and therefore five potential labels (as noted below).

The reason for the multiple labeling is that during the photo-bleaching—structural information is determined. As has been explained above, several images are acquired in order to recover enough information. The multiple labeling (redundancy in the labeling) is beneficial in recovering enough information to generate the final generated image $I_{(reconstructed)}$.

This can be understood from the following example that considers a typical biological preparation. The structural information to be retrieved and the standard labeling and expression protocols can be considered. The following example uses the Brp and Microtubules as described in the examples below. It is expected that 25 Brp molecules form a single T-bar. That means that primary antibodies are binding those antigens with a high degree of specificity. Next polyclonal secondary antibodies are used. Multiple ones of the polyclonal secondary antibodies can bind a single one of the primary antibodies. The secondary antibodies are commercially available antibodies that are labeled with multiple fluorophores. For example Invitrogen Manuals disclose that IgG Alexa whole antibody conjugates have 2-8 fluorophores.

The skilled person will therefore understand that five fluorophores for the label is a reasonable estimate for a standard secondary antibody. Each of the five fluorophores is typically identical, although the skilled person would understand that it would be possible to have different fluorophores. There are therefore estimated to be 250 fluorophores per T-bar. For the microtubules approximately 13 protofilaments form a quasi helical cylinder (25 nm width) with one turn being of 4 nm length. That means that the structural information is 55 nm (25 nm plus the twice the dual secondary antibody length (2*15 nm)). That is roughly 13 turns resulting in 169 antigens. If roughly half of the antigens are available because of microtubule binding proteins, one can expect—approximately 840 fluorophores. If a GFP conjugated microtubule binding protein is used, one can expect 84 of the fluorophores. In the simulations described below between 50 and 100 fluorophores were used. From the way how the labeled biological samples 20 are prepared we can see that the assumption of clusters of fluorophores is reasonable.

Example 1

In-Silico Model

The method of this disclosure was modeled in silico and the method was then tested under several simulated conditions. A model comprising an object of 16 periodically placed fluorescently labeled structures was created. Each of the 16 labeled structures initially comprises 100 fluorophores and is placed at a distance apart from each other of 92% of the diffraction limit as defined by Abbe (0.5λ/NA) (see Abbe E (1873) Contributions to the theory of the microscope and the microscopic perception. Arch Mikr Anat 9:413-468). The justification for modeling with 100 fluorophores is outlined above.

Figure 5:
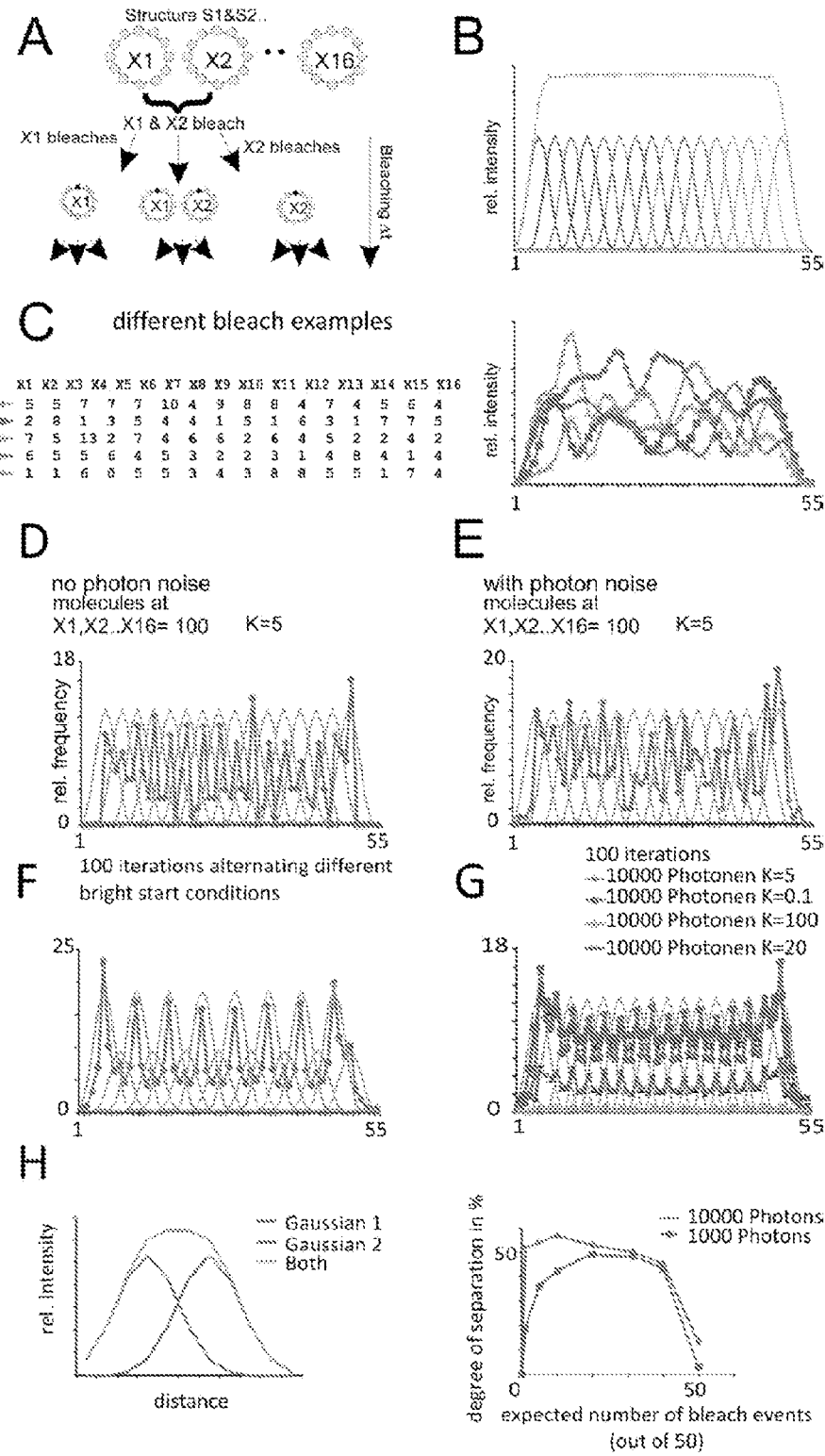
FIG. 5 shows the results of an in-silico model of the method of the present disclosure.

The object comprising the 16 labeled structures was modeled in a one dimensional array of 55 pixels at a mutual distance of 159.9 nm as shown in FIG. 5A. Given that the distance between individual ones of the labeled structures is shorter than the diffraction limit, the simulated point spread functions (PSFs) form a uniform plateau thus hindering the resolution of the individual labeled structures, as shown in FIG. 5B which illustrates the relative intensely over the one dimensional array of FIG. 5A. The PSFs were numerically calculated using the results of Nasset et al (see Nasset M J & Woehl J C (2010). "Realistic modeling of the illumination point spread function in confocal scanning optical microscopy". 1. Opt. Soc. Am. A 27:295-302). The individual ones of the PSFs were normalized such that their integral equals 1. The confocal illumination PSF was used for simplicity and represented 100 fluorophores.

Next stochastic bleaching events (being the photo-physical events in this example) of the fluorophores are simulated during the acquisition of a time series of 100 images. If we assume a constant bleaching rate of the fluorophores located on each of the 16 labeled structures, the probability of the number of bleach events within a period $(t, t+\tau)$ is described by a Poisson process. The photo-bleaching was approximated by subtracting Poisson distributed random numbers from the starting/preceding condition with the expected number being 0.05 times the preceding value, in the case of K=5 at 100 molecules as a starting condition. This is shown in FIG. 5C in which the expected number of bleach events for the first frame is 5 (K=5) and the number of bleached fluorophores at each of the 16 points for five different scans is shown. Typically the differential image will show stochastic peaks of photo-bleaching events. Such non-uniform photo-bleaching peaks will result in detectable intensity maxima in the differential images. The intensity profile that showed a plateau prior to the photo-bleaching (FIG. 5B) now shows peaks and troughs (FIG. 5C, right hand side) upon stochastic photo-bleaching events of the fluorophores. The corresponding differential images thus reveal diffraction limited (photo-bleach) maxima that correspond to the photo-bleaching events in the underlying 16 individual points. The individual (photo-bleach) maxima in the 100 differential images were determined using a sliding maximum detection of 10 neighboring pixels. The differential images were filtered using the top hat filter followed by a Heavyside step function on which negative values are set to zero. Summing the filtered differential images finally reveals the positions of the 16 points that are positioned closer than the diffraction limit (FIG. 5D).

One aspect of the method of the disclosure uses the ability to detect the bleach events in the differential images. To test the contribution of the bleach rate the model of 16 labeled structures imaged in a 55 pixel array was taken and a very low photo-bleaching rate was simulated (less than one fluorophore per frame; K=0.1; mimicking single fluorophore detection approaches) to gradually more simultaneous bleach events (K=5 and K=100). The 16 labeled structures each have 100 fluorophores and the photon noise was set to 10000 photons per fluorophore or, in alternative experiments, to 1000 photons per fluorophore (FIG. 5G). Rather than showing one single example, for each condition the same in silico experiment was iterated 100 times and the average intensities reported ±SEM (FIG. 5G). Independent experiments showed very little variation (the average peak height of the 16 peaks was 11 with maximal SEM on the individual labeled structure being 0.4 for the 10000 photons K=5 case), underpinning the reproducibility.

The data indicate that a very low photo-bleaching rate results in poor resolution as a result of photon noise, while higher photo-bleaching rates fail to resolve the 16 points because too little asymmetry is detected in the differential images. Thus, the ability of the method to resolve structures beyond the diffraction limit is coupled to the photo-bleaching rate of the imaged biological sample 20. In order to assess the range in which the method works the separation of two Gaussian profiles for a given distance placed under the Sparrow limit (50/50 labeling density, 10000/1000 photons) was measured for different bleach rates. FIG. 5H (average of 500 iterations is shown) shows that apart from the extreme values the two structures get better separated over a broad range of the photo-bleaching rates. Note that the value of separation can vary from the actual distance shifting the curve on the y-axis.

To approximate the resolution limit of the method of the disclosure, two structures under the Sparrow criterion were simulated similar to the simulation above using two Gaussian profiles (25/25 labeling density; K~2.1; 10000 photons). Considering a 1.4 NA objective lens and fluorescence emission at 500 nm and by applying the Rayleigh criterion (0.61 NNA, which corresponds to a dip of 20% between the two structures) on the image, the resolution limit in his example can be estimated to be about half of the normal light microscopy resolution (107 nm instead of 218 nm).

Figure 6:
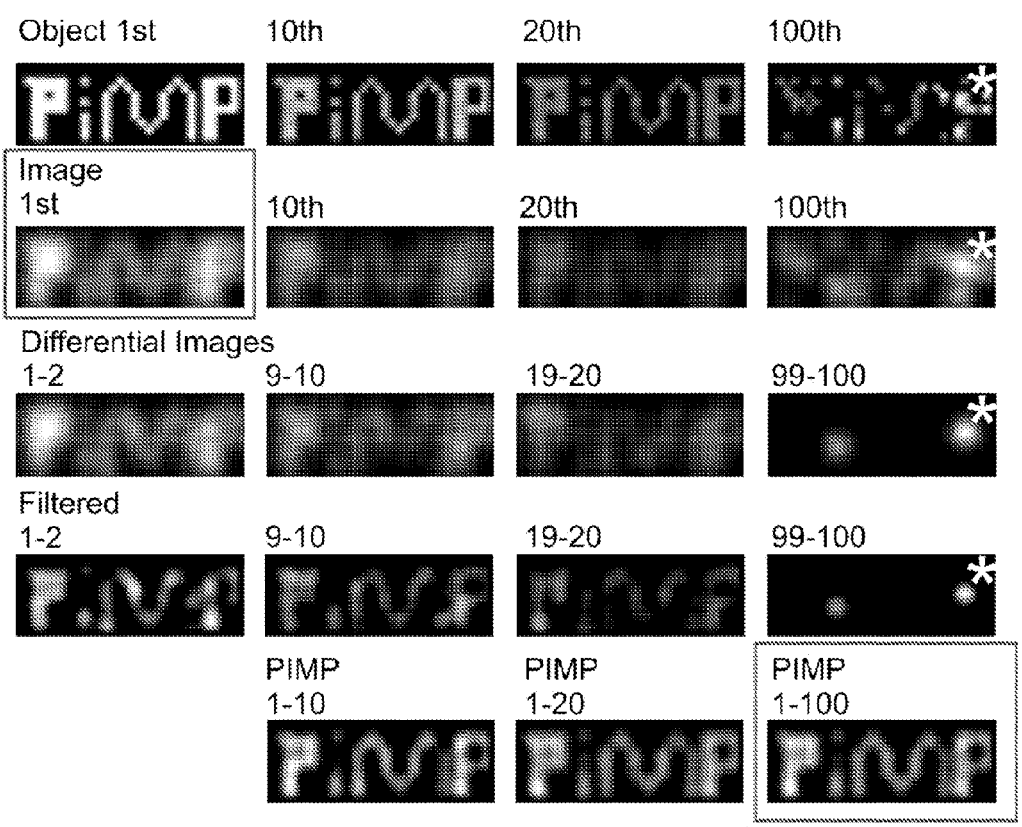
FIG. 6 shows a 2-D test image processed using the method of the present disclosure.

A more complex 2-D test image is shown in FIG. 6 in which the word "PIMP" is photo-bleached and imaged. The first line of FIG. 6 shows the word (object) over time as the word becomes photo-bleached and thus unrecognizable. It will be noted that the intensity of the 100th image has been increased as the $100^{th}$ image would otherwise be effectively invisible.

The second line shows how the word is imaged in a confocal microscope. It will be seen that over time the word becomes blurred. Again the 100th image has had the intensity increased. The third line shows differential images (i.e. differential image of $1^{st}$ and $2^{nd}$ image; differential image between $9^{th}$ and $10^{th}$ image, differential image between $19^{th}$ and $20^{th}$ image and finally the (increased intensity) differential image between $100^{th}$ and $99^{th}$ image). These differential images in the third line have a non-linear variant of the top hat filter applied (negative values were clipped to zero to introduce the non-linearity). The top hat filter used singles out the highest maxima and also takes into account any secondary peaks.

Finally the fifth line shows the use of the method in which in first image (labeled PIMP 1-10) shows the sum of the sequential filtered differential images (i.e., 1-2, 2-3, 3-4, 4-5, 5-6, 6-7, 7-8, 8-9, 9-10). Similarly the second image (labeled PIMP 1-20) includes all of the sequential filtered differential images up to the twentieth image (third image on the second line). The third image (labeled PIMP 1-100) includes all of the sequential filtered differential images up to the $100^{th}$ image (fourth image on the second line). This example shows that the method of the disclosure allows recovery of the information relating to the word even if the raw images are blurred.

It is also conceivable to pre-process the data relating to the images, for example by bandpass filtering or Wiener filtering. The pre-processing may enhance the visibility of the bleaching and suppress noise.

Example 2

Figure 3:
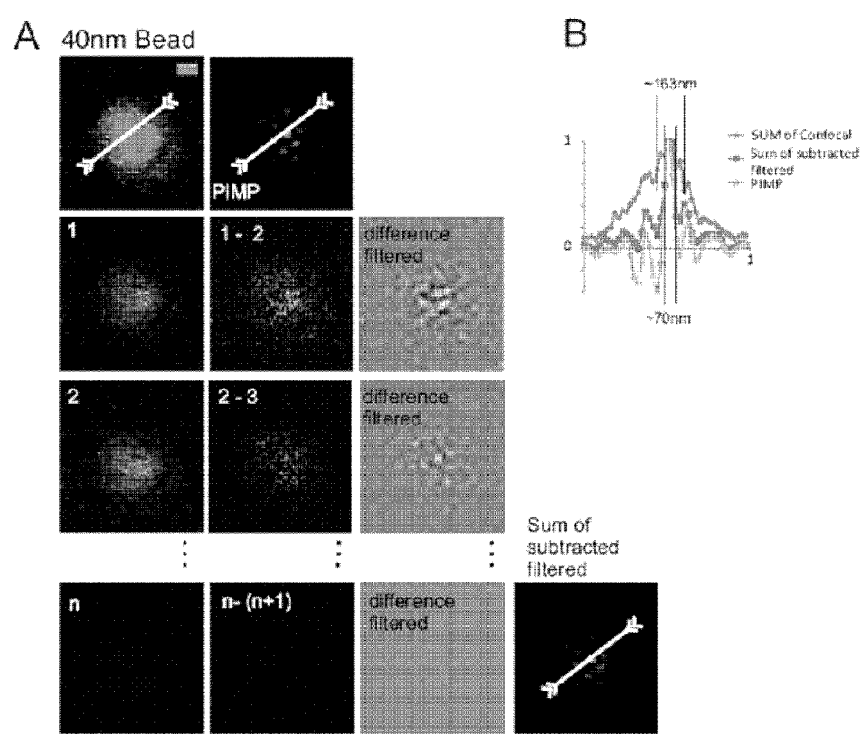
FIG. 3 shows various examples of images created according to a method of the present disclosure.

FIG. 3A shows a further example of the manner in which data is processed in accordance with the present disclosure. The example utilizes as the biological sample 20, 40 nm beads supplied by Invitrogen (Carlsbad, Calif.) emitting at 515 nm. Individual members of the series of images are shown from image 1 to the last image n and include in the first column the original scanned image and in the second column the difference image. The third column shows the filtered difference image.

The fourth row of FIG. 3A (n line) shows that at the end of the time series of n images no fluorescence images are seen. It will be expected that the difference image (third column) reveals nothing of interest. The fourth column of the fourth row of FIG. 3A shows the sum of all of the (n−1) difference images.

FIG. 3B shows normalized intensity distributions for the line profiles indicated by the arrows in the topmost line of FIG. 3A. The full half maximum width (FHMW) is reduced according to the present invention as compared with conventional confocal microscopy. In other words, it can be seen that a 40 nm bead can be observed at 70 nm diameter by the present invention compared to >160 nm when observed by conventional confocal microscopy.

Example 3

Figure 4:
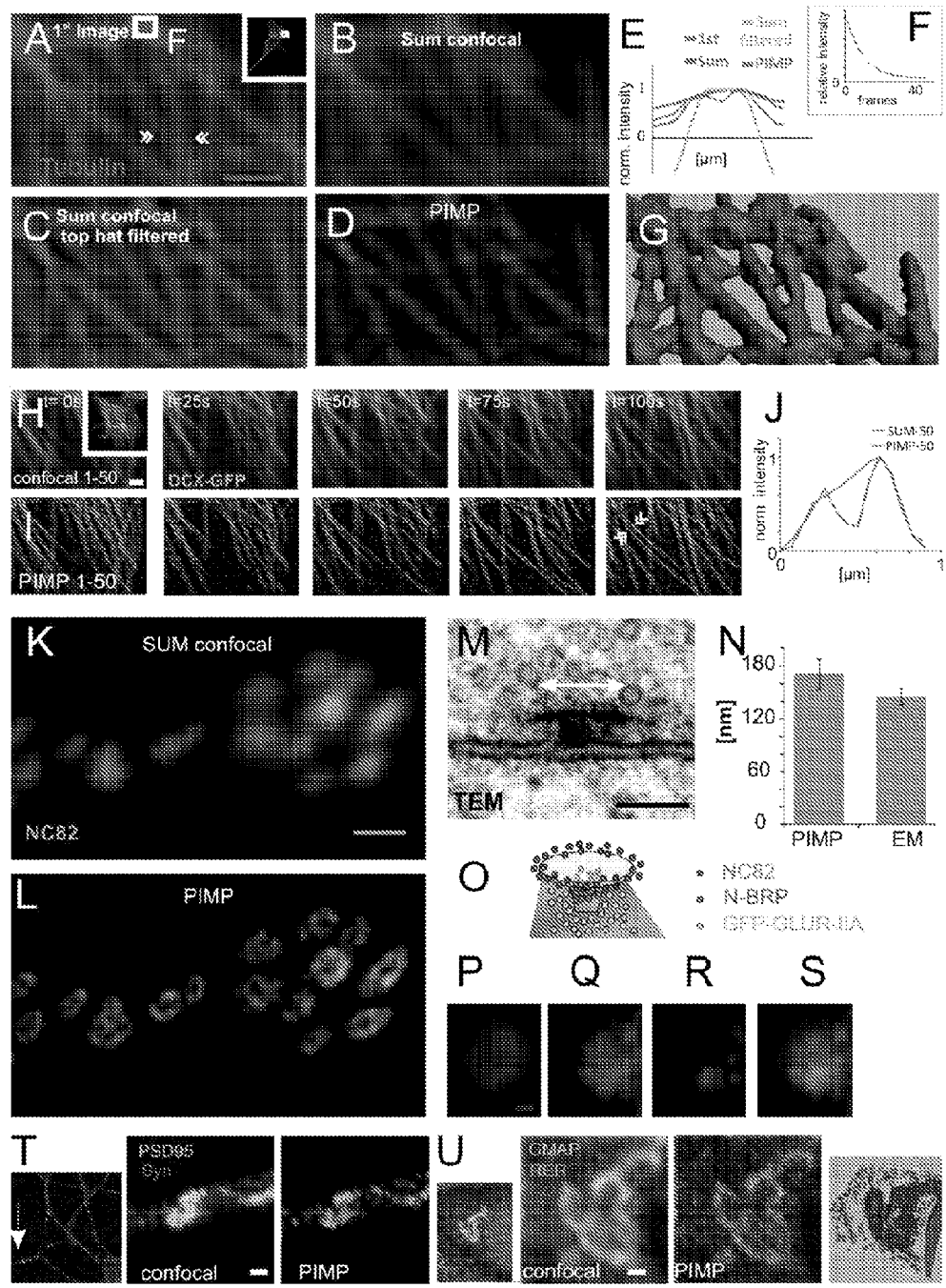
FIG. 4 shows further examples of images created according to a method of the present disclosure.

Microtubules were immuno-labeled in mouse embryonic fibroblasts (MEF) and are illustrated in FIG. 4.

FIG. 4A shows a first image using a confocal microscope and FIG. 4B show a sum of 96 sequential series of images taken using the confocal microscope. FIG. 4C shows the image of FIG. 4B which is filtered using the top hat filter whilst FIG. 4D shows an image obtained using the teachings of this disclosure.

The cells of the immuno-labeled microtubules were scanned 202 times using the confocal microscope 10 which resulted in a progressive bleaching of the biological sample (FIG. 4F). Individual ones of the images were subtracted from each other to produce the differential images and the maxima in the differential images were enhanced using the top hat filter combined with zero clipping of negative values. The summed filtered differential images (FIG. 4D) revealed the labeled microtubules to a higher resolution when compared to a regular confocal image taking using a pinhole corresponding to one Airy (FIG. 4B). The method reveals the microtubules better than the confocal image (FIG. 4B) that is subject to the pre-processing steps used on the differential images (FIG. 4C, 4E). Scanning of the immuno-labeled microtubules at different depths allowed the dissection of a complex three dimensioned sub-cellular organization of the immuno-labeled microtubules (FIG. 4G).

The MEFs were grown in DNEN/FI2 supplemented with 10% FCS, fixed with 4% paraformaldehyde in PBS and processed in direct immunofluorescence. The microtubules in the MEFs were immuno-labeled using mAbs against α-tubulin (mAb DMIA, supplied by Sigma) followed by Alexa-568 conjugated goat anti-mouse secondary antibodies (supplied by Invitrogen). Live ones of the MEFs (see Example 9) were transfected with doublecortin-GFP (form doctor Koester) with Lipofectamin 2000 (from Invitrogen) according to the manufacturer's instructions.

Example 4

The method of the disclosure was applied to a *Drosophila* neuromuscular junction (NMJ) biological sample in order to acquire a time series of images of labeled synaptic active zones (so-called T-bars) immuno-labeled for the active-zone associated Bruchpilot protein (BRP), as known from R. 1. Kittel et al., Science 312, 1051 (19 May 2006).

Third instar wild type *Drosophila* larvae were fixed and processed for immunostaining as described previously by Fouquet et al, in J. Cell Biol. 186, 129 (13 Jul. 2009). Wild-type and mutants expressing GFP-tagged constructs were used. The following antibodies and GFP tagged constructs were used: monoclonal antibody NC82 (mAb NC82) (Developmental Studies Hybridoma Bank, Iowa) recognizing C-terminal BRP; polyclonal antibody BRP-N-term (from S. Sigrist, FU Berlin) recognizing N-terminal BRP (Fouquet et al, in J. Cell Biol. 186, 129 (13 Jul. 2009)) and the GFP-tagged construct UAS-GluRIIA (expresses the GFP-tagged glutamate receptor type IIA without a GAL4 driver) (from S. Sigrist, FU Berlin). Secondary antibodies were conjugated to Alexa-488, Pacific Blue and Alexa-555 (fluorescent dyes from Invitrogen). The laser lines used were the 405 nm for the blue excitation, 488 nm for green excitation and 561 nm for the red excitation.

The labeled synapses were scanned 300 times using a regular confocal microscope at low power (1% of the 150 mW laser module was used in order to provide a low bleaching rate). The microscope used was a Nikon AIR confocal unit mounted on a TI2000 inverted microscope from Nikon Corp. Tokyo, Japan. The microscope was equipped with a Plan Apo 60× oil immersion lens with a N. A. of 1.40. The Plan Apo 60× oil immersion lens is an objective lens that is corrected for several aberrations, planarity of field and chromatic aberrations.

The sequential ones of the time series of images were subtracted to enable the reconstruction of BRP spots with an enhanced resolution as shown in FIG. 4. FIG. 4K shows the results using a conventional confocal laser scanning microscopy and FIG. 4L shows the results according to the method of the present disclosure.

It is clearly observed that the results according to the present disclosure (FIG. 4L) show a ring-like appearance of the BRP-NC82 antigen. In prior art systems the ring-like appearance of the BRP-NC82 antigen could only been visualized by super resolution stimulated emission depletion microscopy (STED) as reported by Kittel et al., Science, 312, 1051 (19 May 2006).

Furthermore a size of the T-bars visualized by transmission electron microscopy (TEM) (see FIG. 4M) agrees very well with the inner-ring diameter measured according to the present disclosure. A comparison of the size of the T-bars visualized by transmission electron microscopy and the present disclosure is shown in FIG. 4N, where the bar PIMP is the result of the present disclosure and the bar EM is the result using transmission electron microscopy. The structure of the biological sample is shown in FIG. 4O. Dissected third instar wild type larvae were processed for TEM as described previously by Kasprowicz et al., J. Cell Biol. 182, 1007 (8 Sep. 2008) and electron micrographs of synaptic boutons and T-bars were obtained using a JEOL 2100 EM microscope operated at 200 kV. The T-bar size was measured as the 'table-top' length of 19 T-bars taken from 3 animals.

For the method of the present disclosure, the ring size of the T-bars as shown in FIG. 4N was measured as inner ring diameter on 19 T-bars.

Example 5

It is possible to use the teachings of the present disclosure to image multiple colors at resolutions in the nanoscopic range.

It is known from W. Fouquet et al., J. Cell Biol. 186 129 (13 Jul. 2009) that BRP orients itself in clusters within the T-bars that are opposite to post-synaptic glutamate receptor clusters. A three-color method was used to distinctly show the labels BRP-N and C-terminal specific antibodies and glutamate-receptor-GFP (see Example 4) and the adjacent domains as shown in FIGS. 4P and 4S. The multiple color method therefore enables the special resolution of macromolecular structures.

FIG. 4O shows a model of the organization of the Bruchpilot protein and the glutamate receptor clusters on the synapse. This model as shown in FIG. 4O was previously proposed and is described in the article of W. Fouquet et al., J. Cell Biol. 186, 129 (Jul. 13, 2009). However the setup as described by W. Fouquet et al., J. Cell Biol. 186, 129 (Jul. 13, 2009) had only one super-resolution channel and the results produced by the W. Fouquet et al. teaching took a long time to determine the structure.

FIGS. 4P, 4Q and FIG. 4R show images of the individual parts of the features that are shown in FIG. 4O.

In FIG. 4S is shown the complete combination of the features as shown in FIGS. 4P, 4Q and 4R with an overlay of the three-color channels used.

In FIG. 4P the NC82 staining of the Bruchpilot protein is shown in which the ring structure is shown as in FIG. 4L. FIG. 4Q shows the glutamate receptors on the postsynaptic side. FIG. 4R shows the N terminal side of BRP.

The results of FIGS. 4A-4G demonstrate that the teachings of the present disclosure can be used for three-color super-resolution measurements and can confirm the earlier described model by W. Fouquet et al. that was worked out using different biological samples with a single super-resolution method. The results of FIGS. 4P, 4A and 4R highlight that more than one color channel can be used by the present disclosure in order to make a multi-color super-resolution image, which demonstrates a versatility of the present disclosure as compared to the prior art methods.

Example 6

The present disclosure allows imaging of the complex micro-tubular network in three dimensions and the results are shown in FIGS. 4A to 4G. FIG. 4A shows a confocal image of the complex micro-tubular network and FIG. 4D shows an image of the complex micro-tubular network according to the present disclosure. The scale bar in FIG. 4A is l/lm (and is also the same value in FIGS. 4A to 4G). In FIG. 4D according to the present disclosure the resolution is clearly greater in comparison to the prior art.

FIG. 4G also illustrates the generation of a 3-D image using the method of the disclosure by combining the images generated by the present disclosure with images generated by conventional confocal laser scanning microscope. The 3-D image is shown in FIG. 4G and is referenced as 3-D-PIMP.

MEF cells were grown in a cell culture medium of DMEM/F12 supplemented with 10% fetal calf serum (FCS), fixed with 4% paraformaldehyde in phosphate buffer (PBS). This was then processed for indirect immunofluorescence. Microtubuli in the MEF cells were immunolabeled using monoclonal antibodies (mAb) against a-tubulin (mAb DMIA, Sigma) followed by Alexa-568 conjugated goat anti-mouse secondary antibodies (Invitrogen). RPE cells were triple immuno-stained for the proteins REP1p, GM130 and GMAP210. Endogenous RER1p resides mainly in the intermediate compartment (IC) (Spasic et al., J. Cell Biol. 176, 629 (2007)) while GM130 and GMAP210 are both localized to distinct sub-domains of the cis-Golgi (Cardenas et al., BMC Biol. 7, 56 (2009). Monoclonal antibody against GM130 and polyclonal antibody GMAP210 were supplied by Biosciences and the group of Cardenas et al., respectively. Purified RER1p polyclonal antibodies (Spasic et al., J. Cell Biol. 176, 629 (2007)) were directly conjugated to Alexafluor-555 (Zenon, Pierce) according to manufacturer's description. GM130 and GMAP210 were labeled using Alexa-488 and Alexa-647 conjugated goat anti-rabbit and anti-mouse secondary antibodies (Invitrogen), respectively.

Example 7

The present disclosure enables the distinction and resolution of pre-synaptic sites from post-synaptic sites in primary hippocampal neurons to be determined as seen with reference to FIG. 4T. Furthermore the teachings of the present disclosure also enable the distinction and resolution of a juxtaposed intermediate compartment and cis-Golgi cisternae in the RPE cells as seen with reference to FIG. 4D. The results according to the disclosure invention are referenced "PIMP" in the figures and the figures according to the prior art are referenced "confocal". It is clear that the figures according to the present disclosure have a greater resolution than the figures generated according to the teachings of the prior art. The RPE cells were grown in a cell culture medium of DMEM/F12 supplemented with 10% fetal calf serum (FCS), fixed with 4% paraformaldehyde in phosphate buffer (PBS).

The primary hippocampal neurons were derived from embryonic day 17 rat embryos (17 days in vitro (DIV)) and cultured in the presence of a glial feeder layer until fully differentiated (21 DIV). Synapses in fixed neurons were immuno-labeled with antibodies against the post-synaptic protein PSD95 (polyclonal antibody (pAb) B102, Invitrogen) and the pre-synaptic synaptophysin (Syn) (mAb derived from clone SVP38, Sigma) and visualized using Alexa-488, and Alexa-568 conjugated goat anti-rabbit and -mouse secondary antibodies. The fluorescent DAPI nucleic acid stain (4',6-diamidino-2-phenylindole) was used to stain nuclei.

Example 8

The method of the disclosure was used for live imaging of slowly evolving processes (time frame: minutes) by over expressing GFP-tagged doublecortin (DCX), a neuronal microtubule binding protein in MEFs (FIG. 4H-4J). Differential images at 0.5 Hz over a period of 25 s were generated, and assigned 50 images to one time point. Within this time point, not all of the fluorophores binding the microtubuli have bleached, and it is likely that new ones of the fluorophores are incorporated that can be used in subsequent time points to generate a bleach series of 50 images (the so-called FRAP effect). Thus, although the time resolution is the minutes range, it is still possible to monitor the growth of the microtubules live and at nanoscopic resolution using the method of the disclosure. The time resolution achievable is largely dependent on imaging speed and on the number of differential images needed to reconstruct the image. However, different than in PALM imaging much fewer one of the images are required for the reconstruction.

Example 9

Figure 7:
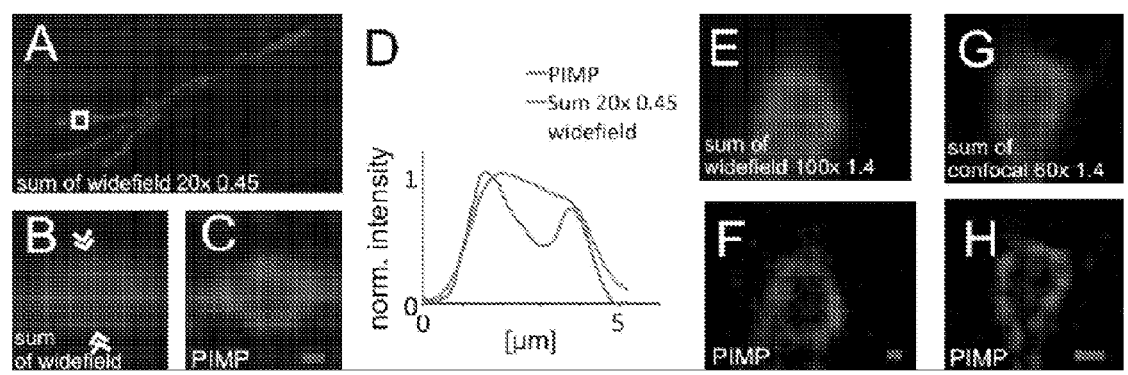
FIG. 7 shows the use of a wide-field microscope with and without the method of the disclosure for the imaging of synaptic boutons of *Drosophila* NMJs.

The previous examples illustrated the method of this disclosure using a confocal microscope 10 with high NA lenses. The post-synaptic marker syndapin at synaptic boutons of *Drosophila* NMJs using different objective lenses and with a wide-field system were imaged. FIG. 7A used a 0.45 NA 20× lens. The wide-field images of the individual boutons appear as field structures. Imaging of the same area numerous times using the same objective lens and camera and processing the data in accordance to the teachings of this disclosure reveal an increase in resolution that allows dissertation of synaptic areas (FIG. 7A-7C).

A 1.4 NA 100× lens was also used (FIG. 7E) and wide-field images of syndapin labeled NMJs were obtained. Imaging under these conditions reveals a post-synaptic accumulation of syndapin label. Processing of the wide-field image for the examples according to the teachings of this disclosure indicate that the syndapin labels concentrate to discrete foci at the apposed-synaptic side akin to other post-synaptically localized proteins including DLG/PSD 95 (FIG. 7F). These findings were confirmed using confocal microscopy (G, 7H).

Example 10

The method of the disclosure can be incorporated into an operating microscope used in a surgical setting. Such operating microscopes typically include components that can be sterilized and thus placeable in substantially direct contact with a live patient. Biological tissues of interest in the live patient can be stained with labels of fluorophores and the stained biological tissues are illuminated with the laser light.

A surgeon is able to view the biological tissues on a monitor and thus remove those unhealthy biological tissues that need to be removed whilst substantially keeping those healthy tissues that do not need to be removed. For example, it is possible to label tumors with emitters. The surgeon is therefore able to remove cancerous tissue whilst leaving healthy tissue in place.

Imaging

All imaging except images acquired in FIG. 7A-F, was performed using a NIKON AIR confocal unit mounted on a Ti2000 inverted microscope (Nikon Corp. Tokyo). The microscope was equipped with a Plan Apo 60× oil immersion (NA 1.40). 0.1/lm microspheres (beads) were imaged using a Radiance 2100 confocal microscope, equipped with a Nikon 1.4 NA oil immersion lens. In FIG. 7A-D a wide field system with a 0.45 NA 20× lens was used (IN Cell Analyzer, GE Healthcare). In FIG. 7E-F a Zeiss upright microscope equipped with a 63×1.4 NA oil immersion lens was used. The Qimaging QICAM camera (Surrey, BC, Canada) and shutter was driven by μManager software. Samples were sequentially imaged using imaging conditions listed in Table 1.

While various embodiments of the present invention have been described above, it should be understood that they have been presented by way of example only, and not limitation. It will be apparent to persons skilled in the art that various changes in form and detail can be made therein without departing from the scope of the invention.

What is desired to be protected by letters patent is set forth in the following claims.

TABLE 1

Imaging conditions and antibody dilutions.
Laser intensity was measured using a Ophir (Ophir Optronics, Jerusalem) Nova laser power meter.

| FIG. | pixel size | scan speed | pixel | pixel dwell time | lasers/Filters | laser power in the object plane in μW | number of frames | Gain (0-255) | primary AB | sec. AB | Dye |
|---|---|---|---|---|---|---|---|---|---|---|---|
| 4 A-G | 55 nm | 4FPS | 128 × 128 | 6.8 μS | 561 nm | 3 | 10 z-sections 96 frames | 80 | 1:300 | 1:1000 | Alexa 568 |
| 4 H-J | 69 nm | 2FPS | 256 × 256 | 3.9 μS | 488 nm | 21.8 | 251/50 | 20 | — | — | GFP |
| 4 K, L | 70 nm | 2FPS | 128 × 128 | 16.5 μS | 488 nm | 1.7 | 200 | 80 | 1:100 | 1:1000 | Alexa 488 |
| 4 P-S | 70 nm | 2FPS | 128 × 128 | 16.5 μS | 405 nm/ 488 nm/ 561 nm | 2.6/1.7/ 5.8 | 114 | 100/80/ 90 | 1:100/ 1:500 | 1:1000/ 1:1000 | Pacific Blue, GFP, Alexa 555 |
| 4 T | 70 nm | 2FPS | 128 × 128 | 16.5 μS | 488 nm/ 561 nm | 1.7/5.8 | 500 | 80/80 | 1:200 PSD/ 1:200 SYN | 1:1000 | Alexa 488, 568 |
| 4U | 70 nm | 4FPS | 128 × 128 | 6.8 μS | 408 nm/ 488 nm/ 561 nm/ 639 nm | 30/4.7/ 56.9/2 | 5 z-sections 50 frames | 80/80/ 90/100 | 1:200 GMAP/ 1:250 RER/ 1:200 GM130 | 1:1000/—/ 1:1000 | Alexa 488, 555, 647 |
| 7 A-C | 370 nm | un-delayed | ccd | 800 ms | Metal Halide 645/30 | — | 100 images separated by 3 s bleach images | — | 1:200 | 1:1000 | Alexa 647 |
| 7 E-F | 115 nm | un-delayed | ccd | 500 ms | Hg Lamp 675/55 | — | 116 | — | 1:200 | 1:1000 | Alexa 647 |
| 7 G-H | 75 nm | 1FPS | 256 × 256 | 9 μS | 639 nm | 2.5 | 53 | 75 | 1:200 | 1:1000 | Alexa 647 |

REFERENCE NUMERALS

10 Microscope
20 Biological sample
30 Objective lens
40 Beam splitter
50 Aperture
60 Light source
65 Light
70 Second Aperture
80 Photo detection device
100 Computer
105 Image processor
110 Image memory
120 Display device
200 Illuminate biological sample
205 Create image
210 Repeat imaging
215 Create difference image
220 Apply filter
225 Generate final image
230 Create 3-D image

What is claimed is:

1. A method for the imaging of labeled biological samples labeled with detectable labels, using fluctuating intensities of radiated light from the biological samples, and comprising:
    illuminating the labeled biological samples to produce the fluctuating intensities of radiated light in the labeled biological samples; and
    localizing the detectable labels, the localizing comprising:

repeatedly collecting light scattered, reflected and fluoresced from the labeled biological sample with a detection device, thereby generating members of a time series of images of the labeled biological samples, wherein at least some of the time series of images illustrate the fluctuating intensities of radiated light;

generating a series of difference images between different pairings of later members of the time series of images and earlier members of the time series of images having the fluctuating intensities of radiated light by subtracting pixel intensities of the earlier members of the time series of images from the later members of the time series of images;

filtering the series of difference images with a filter; and subsequently summing the filtered difference images to generate a final image of the labelled biological samples.

2. The method of claim 1, wherein the filter is one of a high pass, Top-hat or Mexican-hat filter.

3. The method of claim 1, wherein the illumination is provided by laser illumination.

4. The method of claim 1, wherein the labeled biological sample is labeled with a fluorophore.

5. The method of claim 1, further comprising scanning the labeled biological samples to generate one of the members of the time series of images.

6. The method of claim 1, wherein the generating of the plurality of difference images comprises the generating of the difference images between sequential members of the time series of images.

7. The method of claim 1 further comprising combining the final image with a 3-D image of the labeled biological sample to generate a composite 3-D image.

8. An apparatus for the imaging of labeled biological samples labeled with detectable labels, using fluctuating intensities of radiated light from the biological samples, and comprising:
an illumination source for illuminating a portion of the labeled biological sample to produce the fluctuating intensities of radiated light in the biological sample;
a detection device for detecting radiation from the labeled biological sample;
a computer adapted to localize the detectable labels and to generate a final image of the labeled biological samples, the computer including
an image memory for storing members of a time series of images generated by the detection device by repeatedly collecting light scattered, reflected and fluoresced from the labeled biological sample, wherein at least some of the time series of images illustrate the fluctuating intensities of radiated light; and
an image processor adapted to generate a plurality of difference images between later members of the time series of images and earlier members of the time series of images having fluctuating intensities of radiated light by subtracting pixel intensities of the earlier members of the time series of images from later members of the time series of images, each of said plurality of difference images being generated from a different pairing of members of said time series of images, wherein said image processor includes a filter for filtering the plurality of difference images, and the image processor is adapted to subsequently sum the filtered difference images to generate the final image of the labeled biological sample.

9. The apparatus of claim 8, wherein the illumination source is a scanning laser.

10. The apparatus of claim 8, wherein the detection device is a charge-coupled device.

11. The apparatus of claim 8, wherein the radiation from the labeled biological sample is fluorescent radiation.

12. The apparatus of claim 8, wherein the image processor is adapted to apply a filter to the difference images.

13. The apparatus of claim 8 further comprising a display device for displaying the final image.

14. A computer program product comprising a non-transitory computer readable medium having control logic stored therein for causing a microscope to execute a method for the imaging of labeled biological samples labeled with detectable labels, using fluctuating intensities of radiated light from the biological samples by:
illuminating the labeled biological samples to produce the fluctuating intensities of radiated light in the labeled biological samples; and
localizing the detectable labels, the localizing comprising:
repeatedly collecting light scattered, reflected and fluoresced from the labeled biological sample with a detection device, thereby generating members of a time series of images of the labeled biological samples, wherein at least some of the time series of images illustrate differing results of the fluctuating intensities of radiated light;
generating a plurality of difference images between later members of the time series of images and earlier members of the time series of images having fluctuating intensities of radiated light by subtracting pixel intensities of the earlier members of the time series of images from the later members of the time series of images, each of said plurality of difference images being generated from a different pair of members of the time series of images; and
filtering the plurality of difference images with a filter; and
subsequently summing the filtered difference images to generate a final image of the labelled biological samples.

15. A method for the identification of tumor cells samples using fluctuating intensities of radiated light from the biological samples comprising:
labeling the tumor cells with a detectable label to form the labeled biological sample;
illuminating the labeled biological sample to produce the fluctuating intensities of radiated light in the labeled biological sample;
localizing the detectable labels, the localizing comprising:
repeatedly collecting light scattered, reflected and fluoresced from the labeled biological sample with a detection device, thereby generating members of a time series of images of the labeled biological sample, wherein at least some of the time series of images illustrate differing results of the fluctuating intensities of radiated light;

generating a series of difference images between later members of the time series of images and earlier members of the time series of images having differing fluctuating intensities of radiated light by subtracting pixel intensities of the earlier members of the time series of images from the later members of the time series of images;

filtering the series of difference images with a filter; and subsequently summing the filtered difference images to generate a final image of the labeled biological sample; and examining the final image of the labeled biological sample to identify at least one tumor cell in the labeled biological sample.

* * * * *